United States Patent
Pesachovich et al.

(10) Patent No.: US 6,255,526 B1
(45) Date of Patent: *Jul. 3, 2001

(54) PREPARATION OF GABAPENTIN

(75) Inventors: Michael Pesachovich, Givat Shmuel; Claude Singer, Kfar Saba; Gideon Pilarski, Holon, all of (IL)

(73) Assignee: Teva Pharmaceutical Industries Ltd., Petah Tiqva (IL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 26 days.

(21) Appl. No.: 09/331,555
(22) PCT Filed: Dec. 24, 1997
(86) PCT No.: PCT/US97/23164
  § 371 Date: Jan. 14, 2000
  § 102(e) Date: Jan. 14, 2000
(87) PCT Pub. No.: WO98/28255
  PCT Pub. Date: Jul. 2, 1998

(30) Foreign Application Priority Data

Dec. 24, 1996 (IL) .......................................................... 119890

(51) Int. Cl.[7] .................................................. C07C 61/06
(52) U.S. Cl. ............................................................ 562/507
(58) Field of Search ............................................. 562/507

(56) References Cited

U.S. PATENT DOCUMENTS

| 4,024,175 | 5/1977 | Satzinger et al. . | |
| 4,894,476 | 1/1990 | Butler et al. | 562/504 |
| 4,960,931 | 10/1990 | Butler et al. . | |
| 5,068,413 | 11/1991 | Steiner et al. . | |
| 5,095,148 | 3/1992 | Mettler, et al. | 562/507 |
| 5,132,451 | 7/1992 | Jennings et al. | 562/507 |

*Primary Examiner*—Michael L. Shippen
(74) *Attorney, Agent, or Firm*—Kenyon & Kenyon

(57) ABSTRACT

There is disclosed a method of converting gabapenting hydrochloride substantially free of inorganic salts to gabapenting form II. The method comprises the steps of: (1) obtaining gabapentin hydrochloride that is substantially free of inorganic salts; (2) mixing a solution of the gabapenting hydrochloride with an additional amine in a first solvent so as to obtain a precipitate comprising gabapenting; and then (3) recovering gabapentin form II from the precipitate. The precipitated gabapentin is a novel polymorphic form of gabapentin possessing a crystalline structure characterized by novel sets of peaks in the powder X-ray diffraction pattern and in the FTIR spectra. This newly disclosed polymorph of gabapentin is characterized herein as gabapentin form III. The recovery step may comprise, for example, one of two alternative methods, slurrying the gabapentin form II in methanol, and then filtering the suspension to obtain gabapentin form II, or solubilizing the gabapentin form III in methanol with heating by reflux, and then cooling the solution to obtain gabapentin form II by crystallization.

19 Claims, 7 Drawing Sheets

PREPARATION OF GABAPENTIN

FIELD OF THE INVENTION

This invention relates to a new process for converting gabapentin hydrochloride salt to gabapentin via a novel polymorphic form of gabapentin.

BACKGROUND OF THE INVENTION

Gabapentin is 1-(aminomethyl)-1-cyclohexaneacetic acid, having the chemical structure:

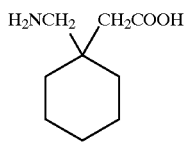

Gabapentin is used in the treatment of cerebral diseases such as epilepsy. The literature describes many ways of preparing gabapentin from a variety of starting materials. U.S. Pat. No. 4,024,175 describes at least three methods of preparing gabapentin from cyclohexyl-1,1-diacetic acid. Each of these methods results in the formation of gabapentin hydrochloride salt, which may be converted to 1-(aminomethyl)-1-cyclohexaneacetic acid by treatment with a basic ion exchanger and then crystallized from a solvent such as ethanol/ether.

U.S. Pat. No. 4,894,476 specifically discloses an improved method for converting the hydrochloride salt into the free amino acid. This involves pouring a deionized water solution of the salt over an ion exchange column, eluting with deionized water, producing a slurry from the eluate, adding an alcohol to the slurry, centrifuging and drying the slurry to obtain the free amino acid.

Alternative methods for preparing gabapentin have been described that do not proceed via the hydrochloride or any other mineral acid salt. Such methods include those described in U.S. Pat. Nos. 5,132,451, 5,095,148, 5,068,413. Each of these methods involve a cyanic intermediate which is hydrogenated under severe conditions to produce the free amino acid.

These methods are industrially impractical. Those methods comprising ion exchange columns require the use of large amounts of ion exchanger for lengthy periods of time to lower the level of chloride ions to the desired level. The alternative methods involve further more demanding steps.

Commercially available gabapentin is crystalline and exhibits an X-ray diffraction pattern with peaks of 2-theta values at 7.8, 13.3, 15.0, 17.0, 20.4, 21.3, 23.1, 23.6, 25.7, 27.0 and 28.2 degrees. Hereinafter, the commercially available polymorphic form of gabapentin is referred to as polymorph form "II".

SUMMARY OF THE INVENTION

The present invention relates to an improved method for purifying gabapentin comprising converting gabapentin hydrochloride salt to gabapentin form II. The present invention avoids the disadvantages associated with prior art methods, by adding alternative steps and by proceeding via a novel polymorphic form of gabapentin.

Accordingly, the present invention relates to a method of converting gabapentin hydrochloride salt to gabapentin form II, comprising reacting a solution of gabapentin hydrochloride with an additional amine in a first solvent to produce a novel polymorphic form as a precipitate, thereafter, converting the novel polymorphic form to form II by forming a suspension and/or a solution of the precipitate in methanol, and then recovering gabapentin form II.

The present invention further relates to a novel polymorphic form of gabapentin designated as gabapentin form III. The polymorph may be identified by its unique X-ray diffraction pattern.

A further aspect of the present invention relates to the novel polymorphic form of gabapentin that is of use as an intermediate in the preparation of polymorphic form II.

Further objectives and advantages of the subject invention will be apparent to those skilled in the art from the detailed description of the disclosed invention.

DETAILED DESCRIPTION OF THE PREFERRED EMBODIMENTS

Figure 1:
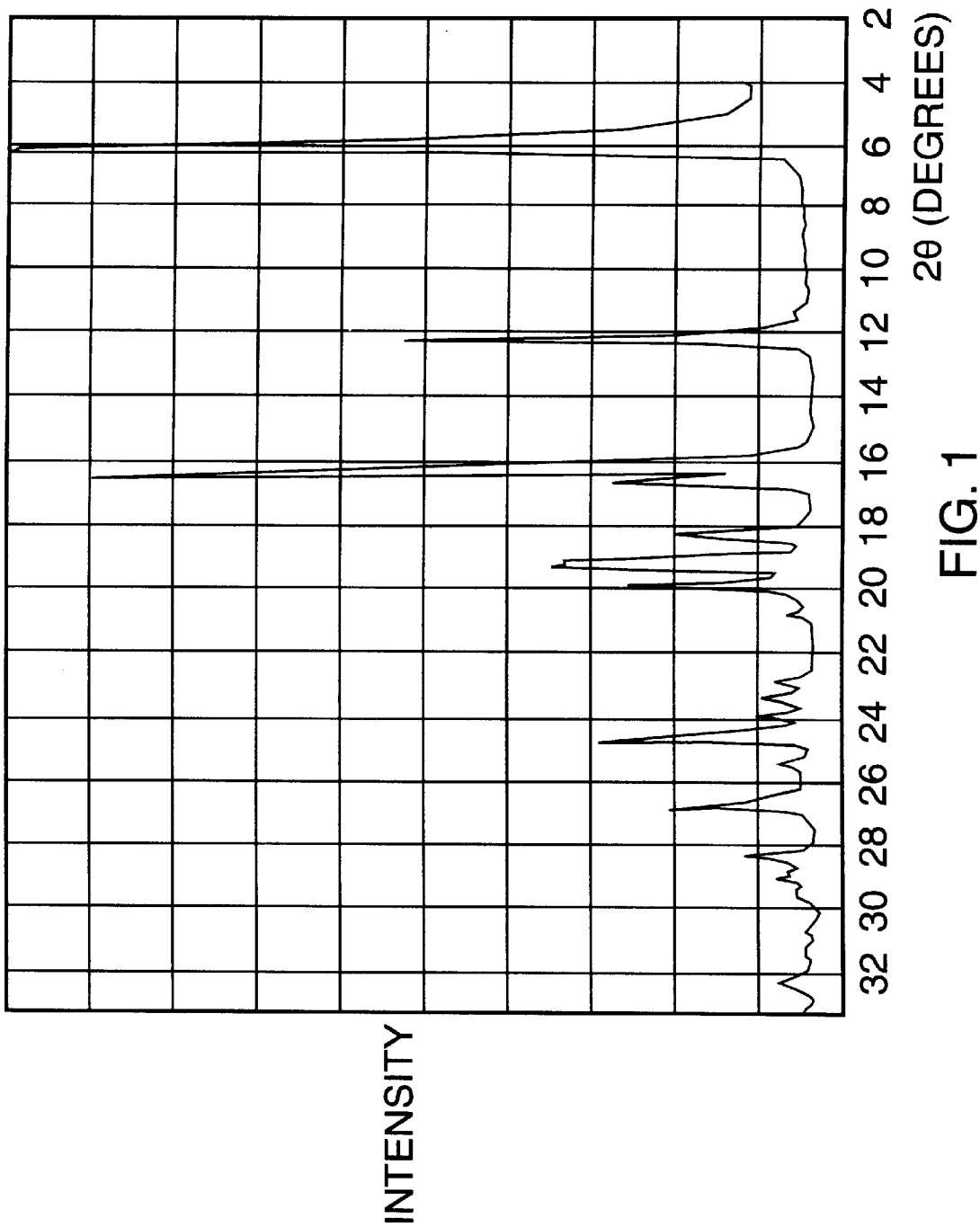
FIG. 1 is an x-ray diffraction pattern of a sample of gabapentin hydrate.

The subject invention will now be described in detail for specific preferred embodiments of the invention, it being understood that these embodiments are intended only as illustrative examples and the invention is not to be limited thereto.

The method of the present invention comprises:
(1) obtaining gabapentin hydrochloride that is substantially free of inorganic salts;
(2) mixing a solution of the gabapentin hydrochloride with an additional amine in a first solvent so as to obtain a precipitate comprising gabapentin; and then
(3) recovering gabapentin form II from the precipitate.

Preferably, the gabapentin hydrochloride used as a starting material in the process of the present invention is substantially free of other inorganic salts such as sodium chloride and sodium bromide, that is, such impurities are only present in trace amounts. Alternatively, gabapentin hydrochloride containing inorganic salts may be used subject to the addition of a further step for removing the inorganic salts prior to mixing gabapentin hydrochloride with the additional amine.

Thus, gabapentin hydrochloride containing inorganic salts may optionally be pre-treated to remove the inorganic salts by the steps of (a) dissolution in a solvent in which gabapentin hydrochloride is soluble, but the inorganic salts are not; (b) filtration of the inorganic salts and, optionally, (c) evaporating the solvent to recover gabapentin hydrochloride substantially free of inorganic salts. Appropriate solvents for the optional pre-treatment step include those selected from the group consisting of methanol, ethanol, n-propanol, isopropanol, butanol, t-butanol, n-butanol, ethyleneglycolmonomethylether, benzylalcohol or dimethylacetamide. Preferably the pre-treatment solvent is identical to the first solvent. This pre-treatment solvent, which is identified in Table 1 and in the claims as the "second solvent", would be used prior to using the "first solvent", if, in fact, this optional pre-treament step is included in the process.

The second step of the present invention comprises mixing a solution of the gabapentin hydrochloride in a solvent that contains an additional amine. The solvent may be any solvent in which the hydrochloride salt of the additional amine is soluble but in which gabapentin form III is insoluble, such that a precipitate of gabapentin form III is formed. Such solvents are preferably selected from the group consisting of ethyl acetate, dimethylcarbonate, ethanol, butanol, t-butanol, n-butanol, methanol, acetonitrile, toluene, isopropylacetate, isopropanol, methylethylketone, acetone, ethyleneglycolmonomethylether, methylene chloride, chloroform, benzylalcohol or dimethylacetamide. The precipitated gabapentin, which may be separated by filtration, is characterized herein as a novel polymorphic form of gabapentin, possessing a crystalline structure characterized by peaks in the powder X ray diffraction pattern with 2-theta values at 6.11, 12.22, 17.00, 18.20, 19.94, 20.81, 24.54, and 25.11 degrees, all ±0.2 degrees. The x-ray diffraction pattern in the samples obtained appears to show a preferred orientation in which the peak at 6.11 degrees is larger than any other peak in the pattern, and the peaks at 12.22 and 24.54 degrees are larger than any of the remaining peaks in the pattern. This polymorph is referred to herein as gabapentin form III.

Two representative embodiments of the third step of the present invention, recovery of gabapentin form II from the precipitate, are slurrying and crystallization. Slurrying may be performed by suspending the precipitated gabapentin in methanol by mixing, stirring, and/or providing continuous agitation with some mechanical device so as to induce transformation into the gabapentin form II that is the commercially available polymorphic form of gabapentin. Gabapentin form II may then be filtered off and washed.

Alternatively, the precipitated gabapentin may be crystallized from methanol with heating by reflux until dissolved, cooling, optionally seeding with gabapentin, followed by further cooling, and then collecting and drying the crystals of gabapentin form II. Second and multiple crops may be obtained from the concentrated mother liqueurs.

Suitable amines for use in the present invention include triethylamine, tributylamine, tripropylamine, trihexylamine, diethylamine, ethanolamine and benzylamine. Preferably the amine is tributylamine.

The form II gabapentin obtained by the methods of the present invention may be crystallized using processes known in the art.

Certain specific representative embodiments of the invention are described in detail below, the materials, apparatus and process steps being understood as examples that are intended to be exemplary and illustrative only. In particular, the invention is not intended to be limited to the methods, materials, conditions, process parameters, apparatus and the like specifically recited herein.

EXAMPLES

1. Preparation of Gabapentin from Gabapentin Hydrochloride

A. Removal of Inorganic Salts

Gabapentin hydrochloride containing inorganic salts (NaCl, NaBr), which may be prepared, for example, as shown in U.S. Pat. No. 4,024,175, Example 4, Variant A, was dissolved in 150 ml isopropanol and mixed at 25° C. Active carbon (0.9 g) was added and the suspension mixed for a further 2 hours. The inorganic salts were removed by filtering. The filter cake was washed twice with 15 ml isopropanol and the washings were added to the gabapentin hydrochloride solution.

B. Precipitation of Gabapentin Base; Formation of Gabapentin Form III

The gabapentin hydrochloride solution of part A was concentrated to dryness in vacuum while ensuring that the temperature of the heating bath did not exceed 35° C. 210 ml ethylacetate and 16.5 ml tributylamine were added and the solution was mixed for 2 hours at 25° C. The gabapentin precipitate was then separated by filtration, the filter cake being washed with 20 ml ethylacetate and then 20 ml methanol. The filter cake contained gabapentin form III which when dried displayed a characteristic X-ray diffraction pattern with 2-theta values at 6.1, 12.2, 17.0, 17.7, 18.3, 20.0, 20.8, 24.6 and 25.5 degrees.

C. Alternative Methods for Conversion of Precipitated Gabapentin to Gabapentin Form II (1) Slurrying The still humid filter cake from step 2 was suspended in 52.5 ml methanol for about 14 hours at 25° C. Solid gabapentin was then separated from the suspension by filtration. The filter cake was washed with 20 ml methanol and then dried under vacuum at 35° C. 10.8 g crystalline gabapentin form II (yield 72%) was obtained.

(2) Crystallization

The still humid filter cake from step 2 was suspended in 210 ml of methanol and the suspension was heated to reflux (65° C.). If dissolution was incomplete, additional methanol was added.

After dissolution, the reactor content was cooled to 34° C. at which temperature crystallization was induced by seeding with pure Form II gabapentin base (0.1 g).

After maintaining the mixture at 34° C. for 60 minutes the reactor content was cooled to 25° C. and methanol was distilled by vacuum distillation. Approximately 160 ml of methanol was collected. Then the suspension was cooled to 0–10° C. and maintained at this temperature for 2 hours.

The crystalline gabapentin was separated by filtration from the suspension. The filter cake was washed with 20 ml methanol and then dried under vacuum at 35° C. 10.8 g of crystalline gabapentin form II (yield 72%) was thus obtained.

Examples 2–20

The method of Example 1 was followed using the slurrying technique of step C(1) and employing the amines and solvents shown in Table 1 below. The percent yields are of purified product except where marked with an asterisk (*), where the yield was measured at the stage prior to the slurrying in methanol.

TABLE 1

Summary of the first solvent, second solvent, amine and yield of examples 2–20.

| Example No. | First Solvent | Second Solvent | Amine | Yield (%) |
|---|---|---|---|---|
| 2 | IPA | IPA | TBA | 61.5 |
| 3 | Et Ac | IPA | TBA | 74.0 |
| 4 | Et Ac | IPA | THA | 66.2 |
| 5 | Et Ac | IPA | TPA | 63.0 |
| 6 | Et Ac | IPA | THA | 79.6* |

TABLE 1-continued

Summary of the first solvent, second solvent, amine and yield of examples 2–20.

| Example No. | First Solvent | Second Solvent | Amine | Yield (%) |
|---|---|---|---|---|
| 7 | IPA Ac | IPA | TBA | 64.9 |
| 8 | ACN | IPA | TBA | 67.8 |
| 9 | DMC | IPA | TBA | 57.9 |
| 10 | DMA | DMA | TBA | 65.7 |
| 11 | BzOH | BzOH | TBA | 43.0* |
| 12 | MEK | IPA | TBA | 88.0* |
| 13 | t-BuOH | t-BuOH | TBA | 79.4* |
| 14 | Acetone | IPA | TBA | 73.1* |
| 15 | Et Ac | BuOH | TBA | 69.8 |
| 16 | MeOH | MeOH | TBA | 67.4 |
| 17 | EGMME | EGMME | TBA | 66.8* |
| 18 | IPA | IPA | TEA | 76.2* |
| 19 | IPA | IPA | BzA | 56.0* |
| 20 | $CH_2Cl_2$ | DMA | DEA | 89.4* |

IPA isopropanol
ACN acetonitrile
BzOH benzyl alcohol
MeOH methanol
$CH_2Cl_2$ methylene chloride
THA trihexylamine
TPA tripropylamine
Et Ac ethyl acetate
MEK methyl ethyl ketone
EGMME ethyleneglycol monomethylether
TBA tributylamine
BzA benzylamine
IPA Ac isopropylacetate
DMC dimethylcarbonate
(t)-BuOH (tert)-butanol
TEA triethylamine The gabapentin form III was characterized by comparing the x-ray diffraction pattern and the FTIR absorption spectra of gabapentin form III with gabapentin form II and gabapentin hydrate. The x-ray powder diffraction patterns of FIGS. 1, 2, and 3a were obtained using a Philips x-ray powder diffractometer with the following parameters:

Goniometer model 1050/70, Cu-tube, Curved graphite monochromator.
Sample holder:
  Quartz monocrystal plate
Settings:
X-Ray tube:
  KV-40
  mA-28
  Target-Cu
  Divergence slit-1°
  Receiving parallel slit-0.2 mm
  Scatter slit-1°
Scintillation detector:
  Voltage-832
  Lower level-33.8%
  Window-34.5%
Scan parameters:
Scanning speed:
  2°/min
Paper speed:
  2cm/min
Gain:
  32
Calibration:
  External calibration with silicon fine powder
Type of radiation:
  copper $K\alpha$.

Figure 3A:
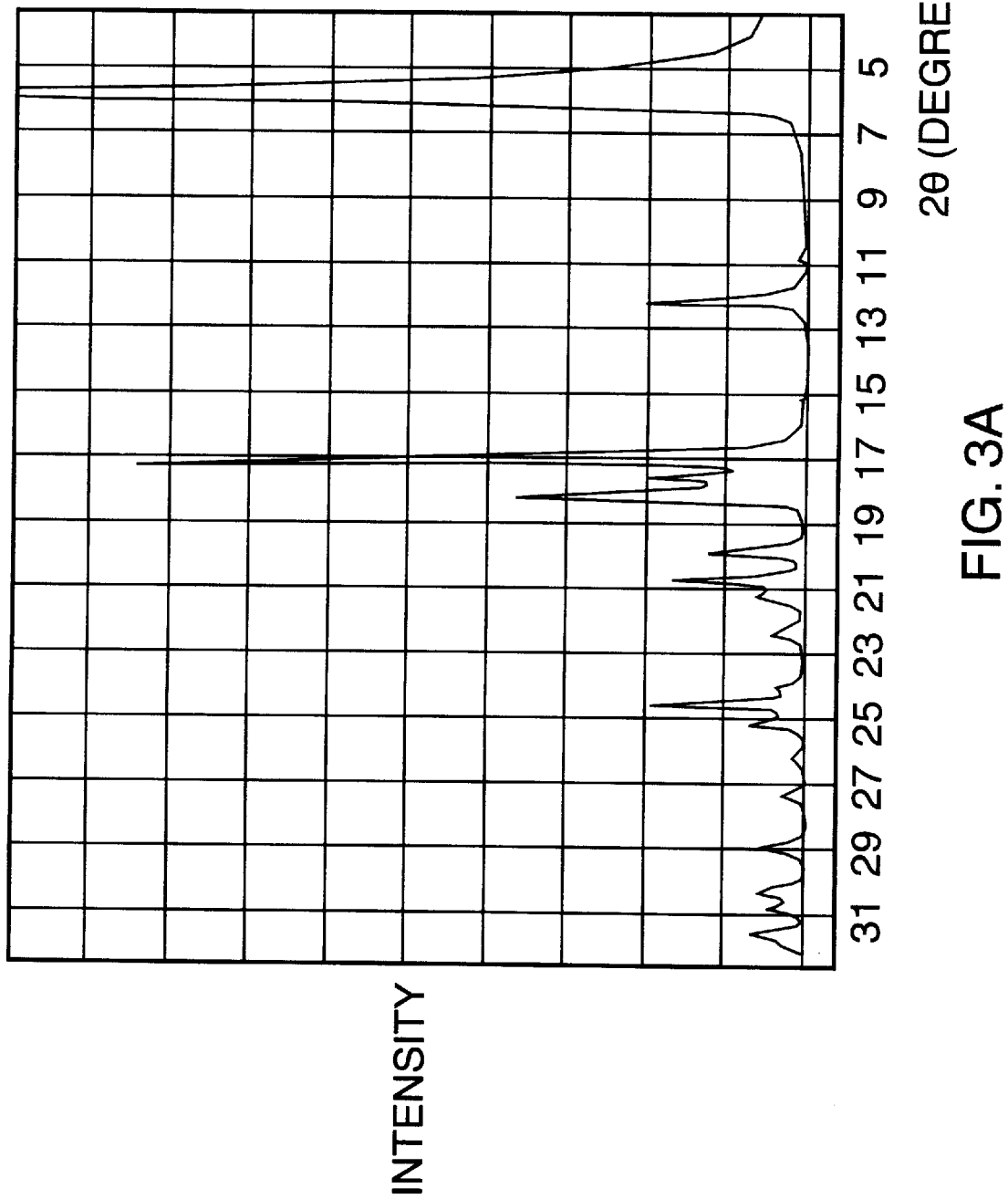
FIGS. 3a and 3b are x-ray diffraction pattern of gabapentin form III, possibly containing small amounts of gabapentin form II and/or gabapentin hydrate.
Figure 3B:
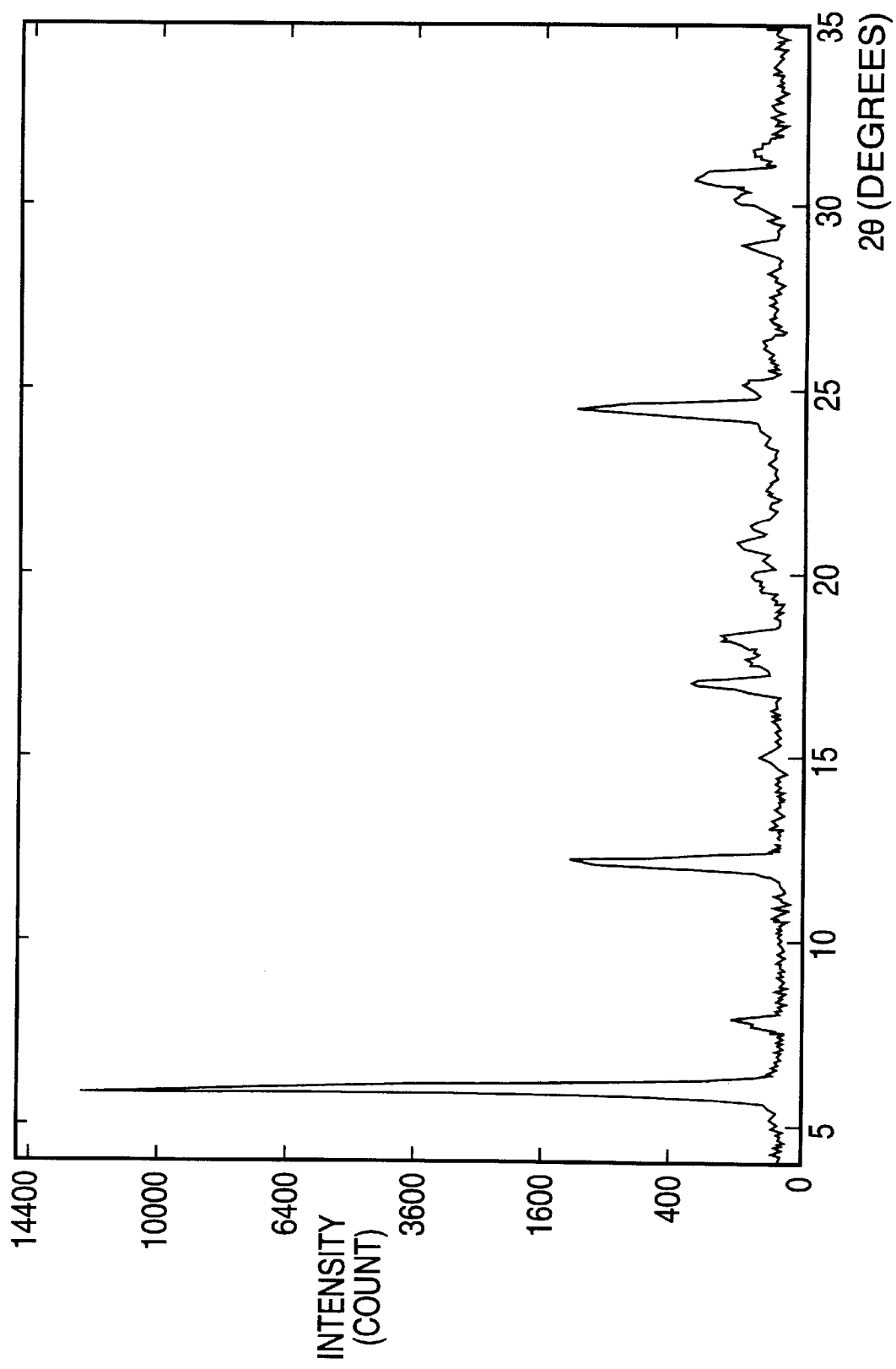

FIG. 3b was obtained using a Siemens B5100 with a presample ($K\alpha_1$ only)monochromator, step scan, Cu radiation, beam slits 0.3, receiving slit 0.05, standard Siemens rotating sample holder, start/stop/step angles in degrees were 4.0, 35, and 0.04, with a step duration of 15 seconds. Standard Siemens D-5000 software was used. The diffractometer was calibrated with NIST large d-spacing standard. No theta-compensating slits were employed.

Figure 2:
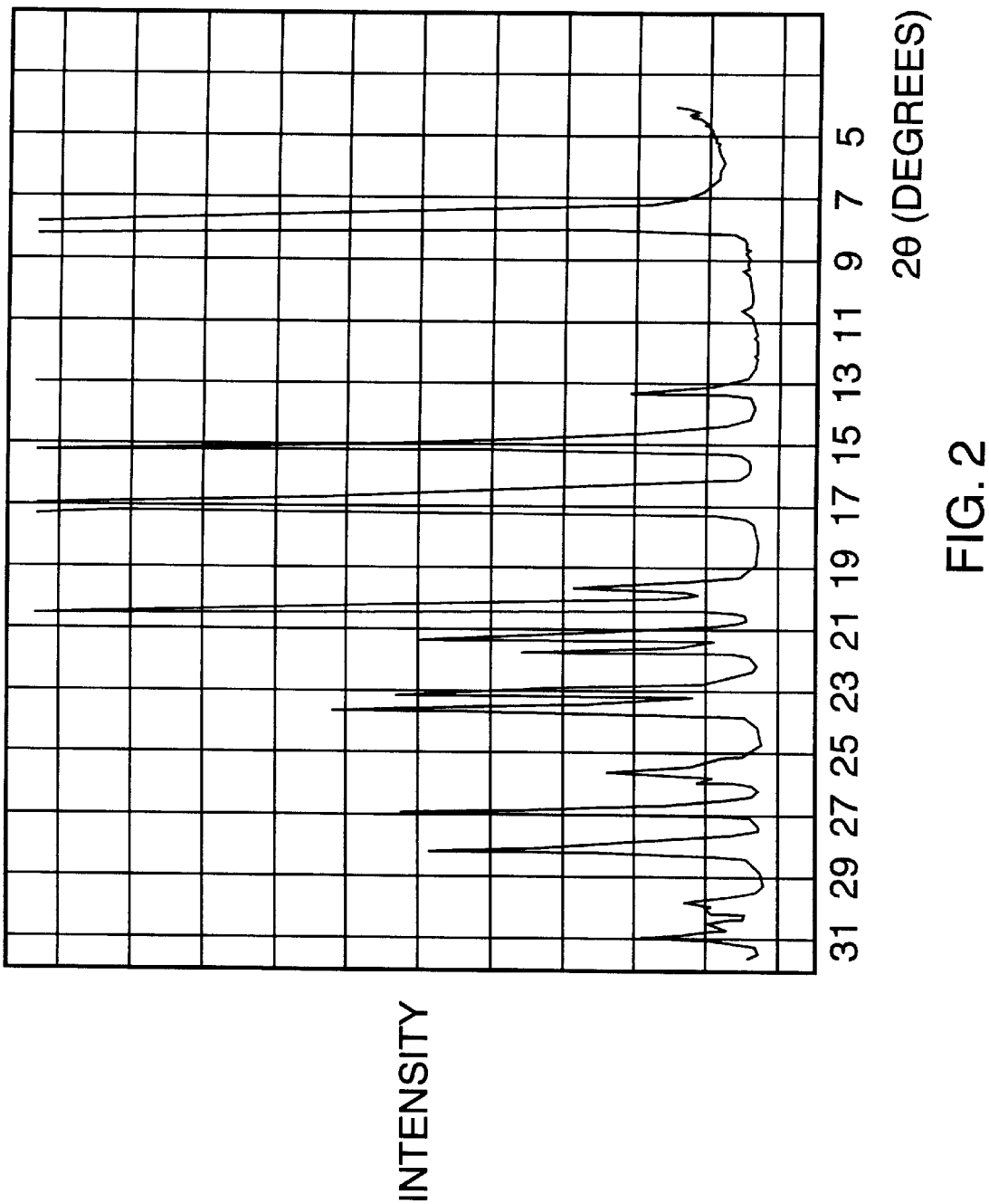
FIG. 2 is an x-ray diffraction pattern of gabapentin form II.

The x-ray spectra of gabapentin hydrate, gabapentin form II and gabapentin form III are shown in FIGS. 1–3, respectively. The main diffraction peaks that characterize each material are listed in Table 2.

TABLE 2

X-ray Diffraction peaks of gabapentin hydrate, gabapentin form II and gabapentin form III.

| Hydrate | Form II | Form III |
|---|---|---|
| 2-theta (°) | 2-theta (°) | 2-theta (°) |
| 6.1 | 7.9 | 6.11 |
| 12.2 | 13.3 | 12.22 |
| 16.0 | 15.0 | 17.00 |
| 18.3 | 17.0 | 17.63 |
| 19.1 | 19.5 | 18.20 |
| 19.8 | 20.3 | 19.94 |
| 20.7 | 21.3 | 20.81 |
| 24.5 | 21.8 | 24.54 |
| 26.4 | 23.0 | 25.11 |
| 28.4 | 23.6 | 28.91 |
| 30.7 | 25.7 | 30.20 |
| 32.3 | 26.9 | 30.78 |
|  | 28.2 | 31.46 |

Figure 4:
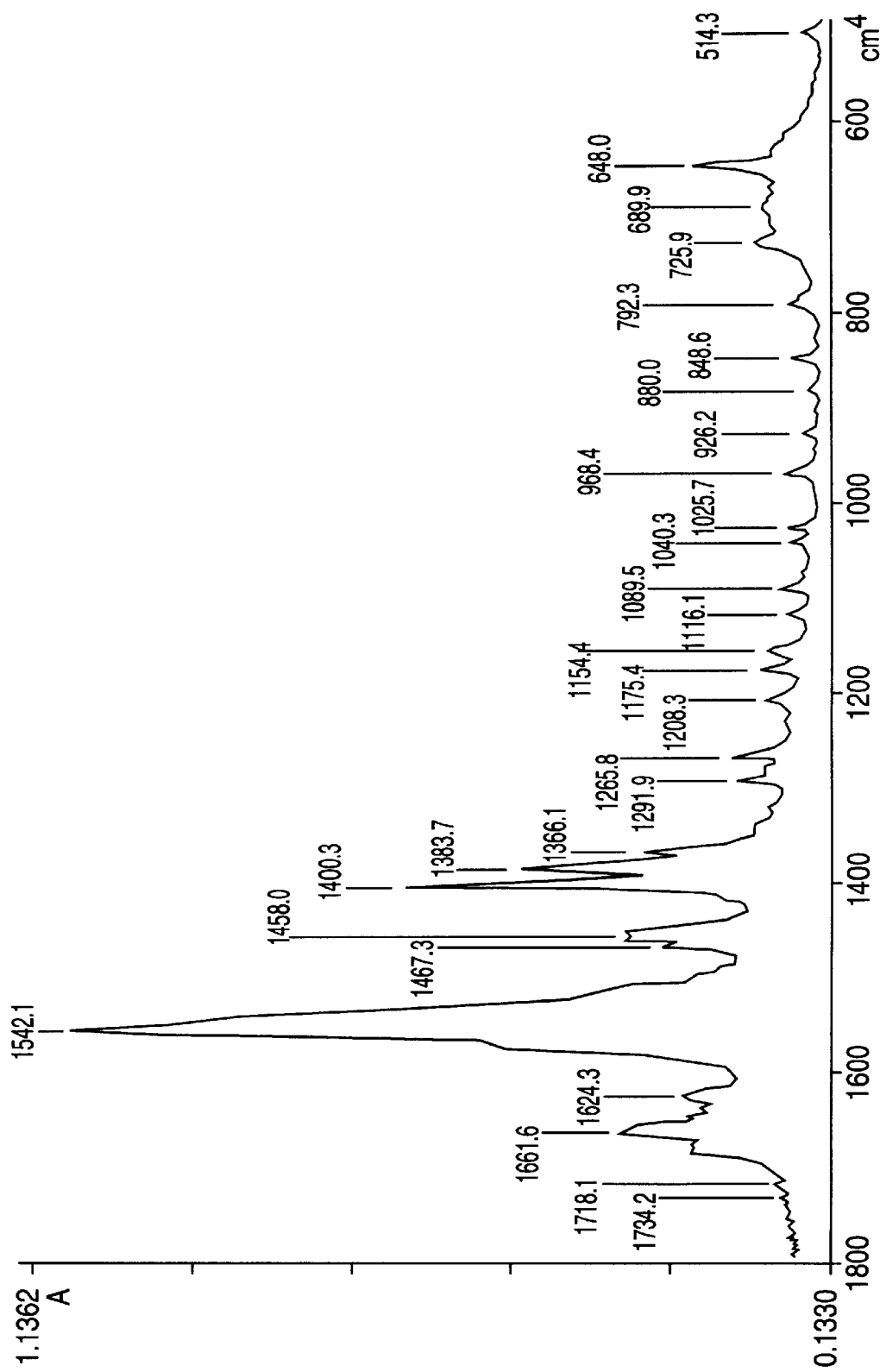
FIG. 4 is an FTIR (Fourier Transform Infra Red) spectrum of gabapentin hydrate.
Figure 5:
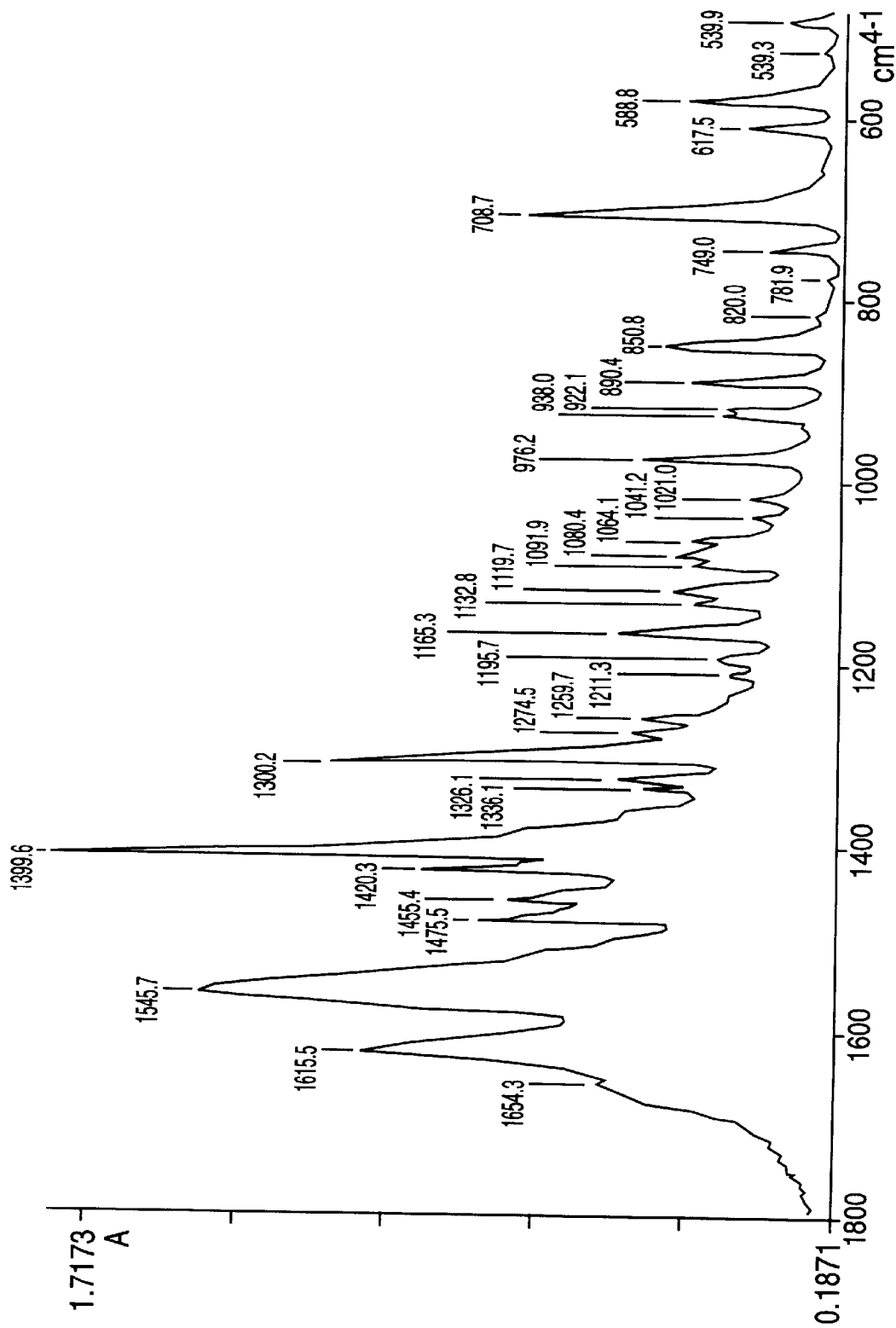
FIG. 5 is an FTIR spectrum of gabapentin form II.
Figure 6:
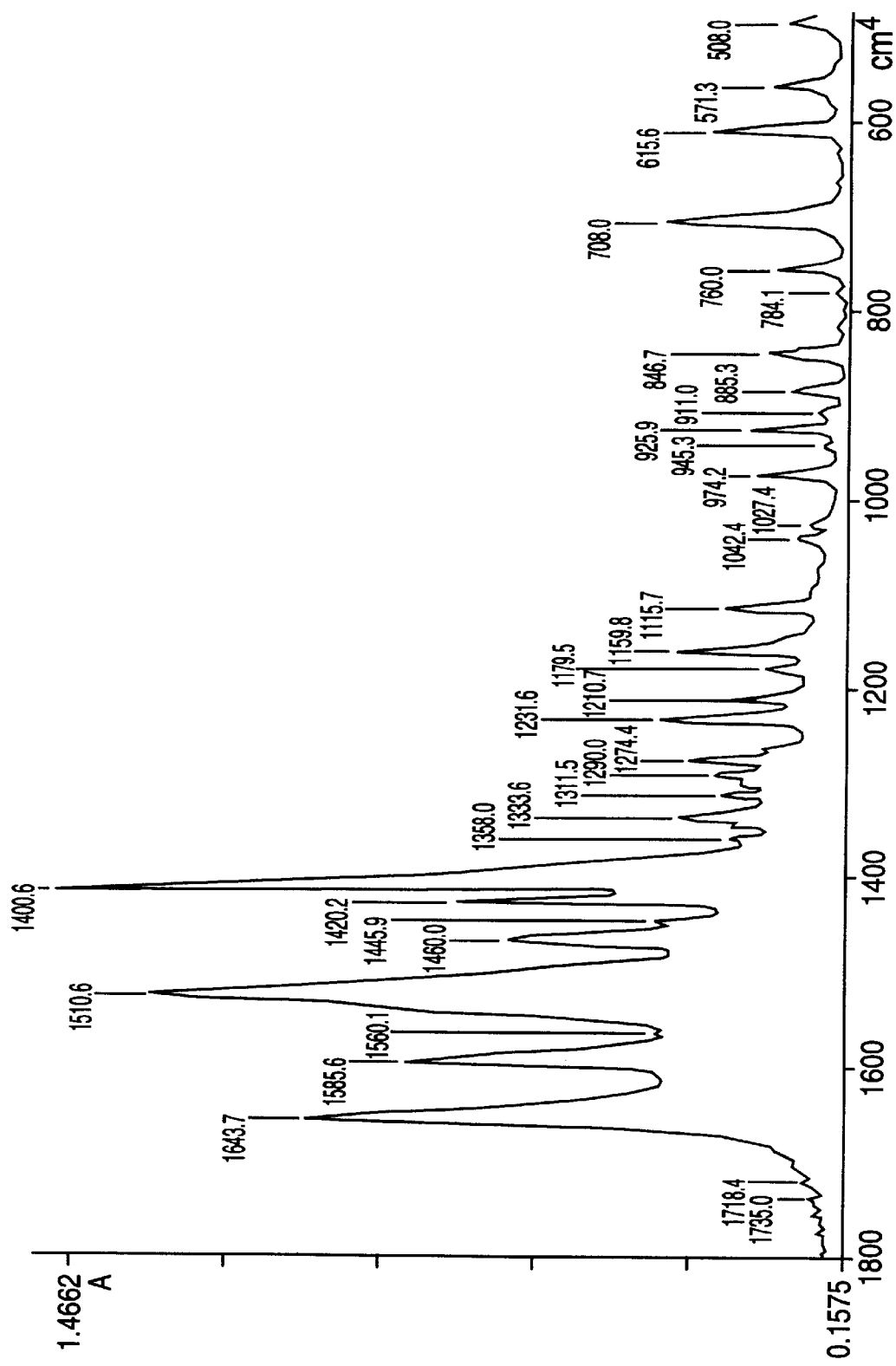
FIG. 6 is an FTIR spectrum of gabapentin form III, possibly containing small amounts of gabapentin form II and/or gabapentin hydrate.

The FTIR spectra for gabapentin hydrate, gabapentin form II and gabapentin form III are shown in FIGS. 4–6, respectively. The FTIR peaks are summarized in Table 3.

TABLE 3

FTIR peaks of gabapentin hydrate, gabapentin form II and gabapentin form III.

| Form I | Form II | Form III |
|---|---|---|
| $cm^{-1}$ | $cm^{-1}$ | $cm^{-1}$ |
| 648 | 709 | 708 |
| 726 | 749 | 760 |
| 880 | 890 | 885 |
| 926 | 922,928 | 926 |
| 968 | 976 | 974 |
| 1154 | 1165 | 1160 |
| 1175 |  | 1180 |
| 1292 | 1300 | 1290 |
|  | 1420 | 1420 |
|  | 1476 | 1460 |
|  |  | 1510 |
| 1542 | 1546 | 1586 |
| 1624 | 1615 | 1664 |
| 1662 |  |  |

Morphology of the three forms:
1. The hydrate form typically exists as large crystals with undefined shapes.
2. Form II typically exists as plate shaped crystals.
3. Form III typically exists as small rhomboidal crystals.

The melting point for gabapentin was not determined since gabapentin decomposes prior to melting.

What is claimed is:
1. A method of converting gabapentin hydrochloride to gabapentin form II comprising:
(1) dissolving gabapentin hydrochloride in a first solvent in which gabapentin is relatively insoluble; and
(2) adding an additional amine to the gabapentin hydrochloride solution so as to obtain a precipitate comprising gabapentin.

2. The method of claim 1, further comprising the step of recovering gabapentin form II from said precipitate.

3. The method of claim 2, the recovering step comprising slurrying or crystallizing said precipitate in methanol.

4. The method of claim 3, wherein said first solvent is selected from the group consisting of ethyl acetate, dimethylcarbonate, ethanol, butanol, t-butanol, n-butanol, methanol, acetonitrile, toluene, isopropylacetate, isopropanol, methylethylketone, acetone, ethyleneglycolmonomethylether, methylene chloride, chloroform, benzylalcohol or dimethylacetamide.

5. The method of claim 1 wherein said additional amine is selected from the group consisting of triethylamine, tributylamine, tripropylamine, trihexylamine, diethylamine, ethanolamine and benzylamine.

6. The method of claim 5 wherein said additional amine is tributylamine.

7. The method of claim 1 wherein said first solvent is selected from the group consisting of ethyl acetate, dimethylcarbonate, ethanol, butanol, t-butanol, n-butanol, methanol, acetonitrile, toluene, isopropylacetate, isopropanol, methylethylketone, acetone, ethyleneglycolmonomethylether, methylene chloride, chloroform, benzylalcohol or dimethylacetamide.

8. The method of claim 7 wherein said first solvent is ethylacetate.

9. The method of claim 1 wherein said first solvent is one in which the hydrochloride salt of said additional amine is soluble.

10. The method of claim 1 further comprising pre-treating said gabapentin hydrochloride to remove inorganic salts, which pre-treatment comprises (a) dissolving gabapentin hydrochloride in a second solvent in which inorganic salts are insoluble, (b) filtering off the inorganic salts, and (c) recovering gabapentin hydrochloride from said second solvent.

11. The method of claim 10 wherein said second solvent is selected from the group consisting of methanol, ethanol, n-propanol, isopropanol, butanol, t-butanol, n-butanol, ethyleneglycolmonomethylether, benzylalcohol or dimethylacetamide.

12. The method of claim 11 wherein said second solvent is isopropanol.

13. The method of claim 1 or 10 wherein the precipitated gabapentin comprises gabapentin form III.

14. The method of claim 10 wherein the precipitated gabapentin comprises gabapentin form III, said second solvent is isopropanol, said first solvent is ethylacetate, and said additional amine is tributylamine.

15. The method of claim 14 wherein said precipitated gabapentin is slurried or crystallized from methanol to yield gabapentin form II.

16. Crystalline gabapentin form III characterized by powder X-ray diffraction peaks at 6.11±0.2, 12.22±0.2, 17.00±0.2, 17.63±0.2, 18.20±0.2, 19.94±0.2, 20.81±0.2, 24.54±0.2, 25.11±0.2, 28.91±0.2, 30.20±0.2, 30.78±0.2, and 31.46±0.2 degrees 2-theta.

17. Crystalline gabapentin form III characterized by powder X-ray diffraction peaks at 6.11±0.2, 12.22±0.2, 17.00±0.2, 17.63±0.2, 18.20±0.2, 19.94±0.2, 20.81±0.2, 24.54±0.2, 25.11±0.2, 28.91±0.2, 30.20±0.2, 30.78±0.2, and 31.46±0.2 degrees 2-theta, wherein the size of the peaks is in the order 6.11 degrees>12.22 and 24.54>17.00, 17.63, 18.20, 19.94, 20.81, 25.11, 28.91, 30.20, 30.78, and 31.46.

18. Crystalline gabapentin form III characterized by infrared absorptions having peaks at 708, 760, 885, 926, 974, 1160, 1180, 1290, 1420, 1460, 1510, 1586, and 1664 cm$^{-1}$.

19. Crystalline gabapentin form III produceable by a process comprising the steps of:

(a) dissolving gabapentin hydrochloride in a solvent selected from the group consisting of ethyl acetate, dimethylcarbonate, ethanol, butanol, t-butanol, n-butanol, methanol, acetonitrile, toluene, isopropylacetate, isopropanol, methylethylketone, acetone, ethyleneglycolmonomethylether, methylene chloride, chloroform, benzylalcohol or dimethylacetamide;

(b) adding an additional amine selected from the group consisting of triethylamine, tributylamine, tripropylamine, trihexylamine, diethylamine, ethanolamine and benzylamine; and (c) drying the precipitated gabapentin.

* * * * *